United States Patent

Bollen et al.

[11] Patent Number: 5,503,853
[45] Date of Patent: Apr. 2, 1996

[54] PROPHYLACTIC AND THERAPEUTIC APPLICATIONS OF PEROXIDASES

[76] Inventors: Alex Bollen, Gaasbeekstraat 65, Brussels; Nicle Moguilevsky, 4 rue P. Delacroix, Brussels B-1150; Michel Pourtois, 23 avenue de la Floride, Brussels, all of Belgium

[21] Appl. No.: 966,069

[22] PCT Filed: Jul. 18, 1991

[86] PCT No.: PCT/BE91/00048

§ 371 Date: Feb. 19, 1993

§ 102(e) Date: Feb. 19, 1993

[87] PCT Pub. No.: WO92/01466

PCT Pub. Date: Feb. 6, 1992

[30] Foreign Application Priority Data

Jul. 19, 1990 [GB] United Kingdom ............... 9015910

[51] Int. Cl.⁶ ......................................... A61K 33/40
[52] U.S. Cl. ..................... 424/607; 514/21; 514/931; 514/934; 514/944; 424/94.1; 424/613; 424/616
[58] Field of Search ..................... 514/21, 931, 934, 514/944; 424/94.1, 607, 613, 616

[56] References Cited

FOREIGN PATENT DOCUMENTS 0361908  4/1990  European Pat. Off. .

OTHER PUBLICATIONS

CA72:76065 (1970).

*Primary Examiner*—Glennon H. Hollrah
*Assistant Examiner*—Brian M. Burn
*Attorney, Agent, or Firm*—Leonard Bloom

[57] ABSTRACT

Prophylactic and therapeutic applications of peroxidases for the manufacture of medicaments for the treatment and prevention and treatment of enveloped virus infections and, in particular, of herpes simplex and immunodeficiency virus infections. The medicaments include a peroxidase, a substrate and a peroxide in a pharmaceutically acceptable carrier. Peroxidases of the medicaments include lactoperoxidase and myeloperoxidase. The medicaments are formulated with a pharmaceutically acceptable carrier for topical, oral and injectable administration to individuals in need thereof.

13 Claims, 4 Drawing Sheets

FIG. 1

FIG. 3
INTRACELLULAR P24 PER $10^6$ CELLS

GROWTH OF HIV-GENERATED P24 IN LYMPHOCYTE CULTURES SOLID LINES (——) : PROINCUBATION 1 HOUR, IN BUFFER ALONE (CONTROLS). STIPPLED LINES (----) : PRO-INCUBATION 1 HOUR, IN OXIDIZING COMPLEX. FINAL DILUTIONS OF HIV INITIAL POOL: 1:20 (● ○); 1:100 (● ○); 1:200 (▲ △).

PROPHYLACTIC AND THERAPEUTIC APPLICATIONS OF PEROXIDASES

FIELD OF THE INVENTION

The present invention relates to prophylactic and therapeutic applications of peroxidases and methods for the prevention and treatment of viral infections and, in particular, to prophylactic and therapeutic applications of peroxidase medicaments, and methods for utilizing such peroxidase medicaments for the prevention and treatment of infections of enveloped viruses, such as the Herpes Simplex Viruses and the Human Immunodeficiency Viruses.

BACKGROUND OF THE INVENTION

The development of effective prophylactic and therapeutic medicaments for preventing and inhibiting the cytotoxic potential of infections of enveloped viruses, and in particular of Herpes Simplex Viruses (HSV's) and Human Immunodeficiency Viruses (HIV's), have proven difficult.

Herpes Simplex Viruses (such as HSV-1 and HSV-2) are widespread. Prophylactic and therapeutic medicaments and methods developed for the prevention and treatment of infections of herpes simplex viruses have, in general, only been partially successful.

Secretions of human milk have long been known to exhibit antiviral activity [see Matthews et al., Lancet, 2: 1388–1390 (1976); Micheals, R. H., J. Immunol., 94: 262–271 (1964); Laegried et al., Acta Paedriatz Scand., 75: 696–701 (1986); and Isaacs et al., J. Infect. Dis., 154: 060–971 (1986)]. In particular, whole human breast milk has "in vitro" been noted to exhibit antiviral neutralizing activity against herpes simplex virus 2. [Lopez et al., Arch. Fr. Pediatr., 46: 263–265 (1989)]. While the origins of this antiviral activity has been attributed to several varying sources, it has never been able to be definitively characterized.

The primary source of the antiviral activity of milk has been attributed to the presence of immunoglobins (IgG's) therein. Other sources that have been suggested as the origin of this antiviral activity includes a non-lipid macromolecule that is relatively stable to heat (Matthews et al., and Micheals, both supra) and/or a molecule having a molecular weight of 400,000 daltons (laegried et al., supra) and/or a component of the lipid layer that effects only encapsulated viruses (issacs et al., supra). This inability to definitely characterize the antiviral origin(s) of milk limits the use thereof, or of components or systems thereof, for antiviral purposes.

Human saliva has also long been known to be active against a number of viruses, including herpes simplex virus 1. [see Gyselink, et al., J. Infect. Dis., 137: 583–586 (1978)]. Unfortunately, the origin of the anti-viral activity of human saliva has not been definitively characterized, being ascribed variously to glycoproteins [Learner, et al., J. Immunol. 96: 59–63 (1966)], immunoglobulin A [Tomasi, J. clin. Invest. 42: 1552–1560 (1963)] or immunoglobulin G (Gyselink, et al., supra). More recently, it has further been suggested that the antiviral activity may be more of a cell-protective activity than a virus neutralizing activity—that is to say, the saliva directly affects the oral epithelial cells, protecting them against infection [see Heineman, H. S., and M. S. Greenberg, Archs Oral Biol. 225: 257–261 (1980)]. Unfortunately, the origin of such activity still remains unknown.

No medicament has been successful in preventing and inhibiting infections of, and the cytotoxic potential of, herpes simplex viruses in all stages.

The human immunodeficiency viruses (HIV's) are fatal and widespread and have only relatively recently been identified. The biochemistry and physiology of these HIV's are poorly known and understood. It has been reported that "in vitro" contact, for at least one-half hour or more, with whole human saliva inhibits the ability of human immunodeficiency virus (HIV) to infect phytohaemagglutinin-stimulated lymphocytes. [Fultz, Lancet, 2:1215 (1986)]. However, shorter periods of incubation have failed to demonstrate an impressive antiseptic effect (see Fultz, supra). Moreover, not all of the saliva samples reported can insure a 100% inhibition of HIV-1 infectivity [see Fox et al., JADA, 118: 709–711 (1989)].

As yet, no medicaments or methods of which we are aware have proven to be consistently successful for preventing and treating infections of, and the cytotoxic potential of, the HIV's.

Other enveloped viruses that are particularly troublesome to effectively prevent and treat include herpes viruses (such as Varicella-zoster virus, cytomegalovirus, Epstein-Barr virus, human herpes virus-6), the paramyxoviruses (such as human parainfluenza viruses), the family of orthomyxoviruses (such as the influenza type viruses A and B), rotaviruses, coronaviruses and retroviruses (such as Human T-cell leukemia virus-1, bovine leukemia virus and simian immunodeficiency virus).

It is well known that natural antimicrobial agents are contained in most natural external mammalian secretions. In particular, the naturally-occurring antimicrobial thiocyanate/peroxidase/$H_2O_2$ systems present in saliva and in milk have been extensively studied.

In saliva, an antimicrobial peroxidase-dependent system has been described which can generate hypothiocyanite (OSCN-), as follows:

$$H_2O_2 + SCN^- \xrightarrow{peroxidases} OSCN^- + H_2O$$

[Oram and Reiter, Biochem. J., 100:373–381 (1966); Hogg and Jago, Biochem. J., 117: 779–790 (1970); and Carlsson et al., Infect. Immun., 44: 581–586 (1984)]. The peroxidases thought to be present in saliva that oxidize thiocyanate in this system include salivary peroxidase and lactoperoxidase. A similar antimicrobial lactoperoxidase-dependent system has also been identified in milk. [Oram and Reiter, Biochem. J., 100:382 (1966)]. Indeed, it has been suggested that the same peroxidase/thiocyanate/hydrogen peroxide system that operates in saliva also operates in milk. [see Klebanoff, S. J., et al., J. Dent Res. (supp.) p.86 (1965).]

The antimicrobial efficiency of the thiocyanate/peroxidase/hydrogen peroxide system has been demonstrated "in vitro" against several bacteria known to be responsible for frequent destruction of teeth and/or periodontium [See Carlsson, supra, and Courtois et al., J. Dent. Res. 68 (spec. issue):1002 (1989)]. The antimicrobial efficiency of this system was also demonstrated "in vivo" in cases of aphtous lesions of the buccal mucosa [Hoogendoorn and Piessens. J. Oral Pathol., 16: 425–427 (1987)].

Unfortunately, the precise antimicrobal mechanism of the thiocyanate/peroxidase/$H_2O_2$ system has not been definitely characterized. However, it is believed that at physiological pH, hypothiocyanite (generated by this system) mediates the oxidation of essential proteins and enzymes sulfhydryls groups of the bacteria, resulting in microbial inhibition.

Additionally, it has been suggested that lactoperoxidase may be responsible for the formation of higher oxyacids of the thiocyanate ion, such as cyanosulfurous and cyanosulfuric acids, which may also be responsible for antimicrobial inhibition. [Bjoerck, L., and O. Claesson, J. Dairy Sci. 63:919–921 (1980); Hogg, et al., supra; and Pruitt, et al., Biochemistry 21:562–567 (1982)].

Antimicrobial dentifrices that contain a thiocyanate/peroxidase/hydrogen peroxide system are known. Upon oral administration, the enzyme-dependent systems in these antimicrobial dentifrices are activated by various components (such as oxygen and/or water) of the natural chemical environment of the oral cavity. In particular, U.S. Pat. No. 4,564,519 issued to Pellico et al., (hereinafter sometimes referred to as Pellico '519) discloses a di-enzymatic chewable orally-activated antimicrobial dentifrice that includes a thiocyanate salt and lactoperoxidase which, through interaction with hydrogen peroxide formed by another enzymatic system in the dentifrice, produces a bacterial inhibitor in the form of a negative, monovalent hypothiocyanite ion (OSCN—) which exists in solution in acid-base equilibrium with hypothiocyanous acid (HOSCN).

Also, in U.S. Pat. No. 4,576,817 issued to Montgomery et al., it was disclosed to provide antimicrobial enzymatic bandages and pads for disinfection purposes. These pads include a serum-activated oxidoreductase enzyme for producing hydrogen peroxide upon contact of the enzymatic materials with serum. In one embodiment, these antimicrobial bandages are formulated to also include a peroxidatic peroxidase, such as lactoperoxidase.

In the journal BIOFUTUR (February, 1990, at page 52), a system is disclosed having two enzymes that, in tandem, generates toxic radicals that may be useful for the treatment of various infections. This system includes glucose oxidase which, in the presence of glucose, generates $H_2O_2$. This system also includes a peroxidase which, with the $H_2O_2$, generates iodides that are highly toxic for the cell. Unfortunately, the precise mechanism of this toxicity is not known. It was further reported therein that this glucose oxidase/peroxidase system has been coupled to a monoclonal antibody against *Candida albicans* and has been found effective for protecting against such infections in mice. This glucose oxidase/peroxidase system has also been coupled to a monoclonal antibody for the epitope of the gp 120 fraction of HIV and has been found to be effective against infections of *Sacharomyces* expressing this epitope.

In the journal CLINICAL RESEARCH, vol. 36, No. 5 (1988) at 809A, a lactoperoxidase-halide-hydrogen peroxide (LHHP) system was reported to be effective, in vitro, on respiratory syncytial virus (RSV) replication. It was also suggested that a myeloperoxidase-halide-peroxidase system (that plays an important role in host defense mechanisms against phagocytosed bacteria) may also have a role in host defense against RSV.

Finally, in PCT patent application, no. WO 8912457, the incorporation of myeloperoxidase with a carrier is disclosed for administration to humans for reinforcing the natural antibody activity thereof at the macrophage level. In this disclosure, purified myeloperoxidase is linked with a carrier that has an affinity for the macrophage, so that the carrier will transport the myeloperoxidase to where it may be captured and utilized by the macrophage for antibody defense. Carriers disclosed include antibodies, or fragments thereof that have an affinity for the macrophages. Other suggested carriers include particular liposomes and human serum albumin. Preferably, the myeloperoxidase and the linked carrier are formed utilizing recombinant DNA technologies. Such a composition is provided to aid, augment and reinforce the bodies natural antibody defenses and is believed to be useful in combatting various infections, including HIV.

Despite the long-standing coexistence of the knowledge of the properties of the peroxidases and the thiocyanate/peroxidase/hydrogen peroxide system, as well as the need for prophylatic and therapeutic medicaments for the prevention and treatment of infections of enveloped viruses (and in particular of herpes simplex and human immunodeficiency viruses), to the best of our knowledge no one has utilized medicaments incorporating such peroxidases or peroxide systems for the prevention or treatment of infections of enveloped viruses and, in particular, for the prevention and treatment of herpes simplex and human immunodeficiency virus infections.

Thus, it can be seen that there remains a need for prophylactic and therapeutic peroxidase medicaments which prevent and/or treat infections of enveloped viruses, including HSV and HIV, and for prophylactic and therapeutic applications of peroxidases in a medicament that may be administered to an individual in need thereof without depending upon naturally-occurring concentrations of substrate, oxygen donors or peroxidases for their inhibitory effect. Finally, there remains a need for methods for the prevention and treatment of infections of enveloped viruses, including HSV's and HIV's, by the administration of prophylactic and therapeutically effective amounts of such peroxidase medicaments to an individual in need thereof.

SUMMARY OF THE INVENTION

It is a primary object of the present invention to provide uses (applications) for peroxidases in the formulation (manufacture) of medicaments for the prevention and treatment of enveloped viruses.

It is another object of the present invention to provide prophylactic and therapeutic applications of peroxidases in medicaments for the prevention and treatment of infections of enveloped viruses, including herpes simplex and human immunodeficiency viruses.

It is still another primary object of the present invention to provide prophylactic and therapeutic methods for viruses, by the administration of prophylactic and therapeutically effective amounts of peroxidase medicaments to individuals in need thereof.

As utilized herein, the term "prophylactic" refers to medicaments, amounts or quantities, methods, uses and effects, etc., that prevent and/or aid in preventing infections of enveloped viruses and, in particular of the HSV's and the HIV's. As utilized herein, the term "therapeutic" refers variously to medicaments, amounts or quantities, methods, uses and effects, etc., that ameliorate infections of enveloped viruses and, in particular of the HSV's and the HIV's.

In accordance with the teachings of the present invention, there are disclosed herein prophylactic and therapeutic applications of peroxidases in medicaments, and methods for the administration of the peroxidase medicaments, for the prevention and treatment of infections of enveloped viruses, including herpes simplex and human immunodeficiency viruses.

The preferred peroxidase medicament (hereinafter sometimes referred to as the "peroxidase composition" or simply as the "composition") of the present invention, is a substantially self-contained antiviral system that may operate without depending upon naturally-occurring "in vivo" compounds, or concentrations thereof, of the user thereof. This medicament includes: an oxygen donor, which is preferably a glucose-glucose oxidase enzymatic system that generates hydrogen peroxide; a peroxidase, such as lactoperoxidase; and a substrate, chosen from a group consisting of halogens and pseudo-halogens. These peroxidase medicaments are formulated, such that comparatively short-term administration thereof is effective for the prevention and treatment of enveloped viruses, such as the HSV's and HIV's. Preferably, the concentrations and/or formulations of these components have been chosen to maximize oxygen donor and peroxidase-generated compound production, while simultaneously maintaining the oxygen donor concentrations at levels which do not interfere with the activity of the peroxidase.

It is noted that it is preferred to formulate the peroxidase medicaments of the present invention, so as to include various components of, and mimic somewhat, the salivary thiocyanate-peroxidase system. Such a formulation is preferred since the components thereof would be genuine components of human external secretions. This formulation is further preferred since the antiviral activity thereof can possibly be further enhanced through the absorption of foods enriched with any of the various components thereof.

Accordingly, the present invention most preferably provides substantially self-contained hypothiocyanite-generating, prophylactic and therapeutic peroxidase/thiocyanate/hydrogen peroxide medicaments that may be applied and utilized without depending upon the users naturally-occurring "in vivo" salivary concentrations thereof, for the prevention and treatment of infections of enveloped viruses.

Other enveloped viruses to be prevented and/or treated by the peroxidase medicaments of the present invention include the paramyxoviruses (such as human parainfluenza viruses), the family of orthomyxoviruses (such as the influenza type viruses A and B), rotaviruses, coronaviruses, herpes viruses (such as Varicella-zoster virus, cytomegalovirus, Epstein-Barr virus and HHV6) and retroviruses (such as Human T-cell leukemia virus-1, bovine leukemia virus and SIV).

Still further accordance with the teachings of the present invention, there is disclosed a method for the prevention and treatment of infections of enveloped viruses, such as herpes simplex viruses and human immunodeficiency viruses. This method involves the administration of prophylactic and therapeutic effective amounts of the peroxidase medicaments of the present invention to an individual in need thereof.

These and other objects of the present invention will become apparent from the following specification, when taken in conjunction with the enclosed figures.

DESCRIPTION OF THE INVENTION

The peroxidase medicaments of the present invention include a peroxidase. Preferably, the peroxidase medicaments include peroxidase/oxidizable substrate/oxygen donor system that exhibits antiviral properties against enveloped viruses, including HSV's and HIV's. In these antiviral medicaments, peroxidase catalyzes oxidation of the substrate (a halogen or pseudo-halogen) by the oxygen donor (a peroxide) to form negatively-charged, monovalent oxidizing compounds. The medicaments may be formulated for prophylactic and/or therapeutically purposes, as desired and needed, for permitting the administration of prophylactic and/or therapeutic effective amounts thereof to an individual in need thereof for preventing and/or treating infections of enveloped viruses, such as the HSV's and the HIV's.

The peroxidase medicaments of the present invention are also useful for prophylactic and therapeutic applications against infections of enveloped viruses, such as paramyxoviruses, the family of orthomyxoviruses, rotaviruses, coronaviruses, herpes viruses (such as varicella-zoster virus, cytomegalovirus, Epstein-Barr virus and human herpes virus-6) and retroviruses (such as human T-cell virus-1, bovine leukemia virus and simian immunodeficiency virus).

The substrate of the medicaments of the present invention is chosen from a group consisting of negatively-charged halogens, and their derivatives, and negatively-charged pseudo-halogens, and their derivatives. The term "halogens" reports to certain of those elements, in their negatively-charged monovalent states, that belong to Group VII of the Periodic Table of Elements and, as is well known to those skilled in the art, includes bromide, chloride and iodide. The term "pseudo-halogens" refers to certain negatively-charged ions and ionic compounds that are monovalent. The "pseudo-halogens" of the present invention include the thiocyanate salts, such as sodium thiocyanate, potassium thiocyanate, ammonium thiocyanate, ferric thiocyanate and mixtures thereof. These substrates and their derivatives are able to be extracted (isolated) from natural material (for example, saliva and human milk) or produced by natural or chemical methods, all of which are well known to those skilled in the art.

The peroxidases in the medicaments of the present invention catalyze the oxidation of the substrate by the oxygen donor for generating the oxidizing compounds. These peroxidases include plant (vegetable) peroxidases, such as horseradish peroxidase, and mammalian peroxidases, such as salivary peroxidases, lactoperoxidases, myeloperoxidases and eosinophil peroxidase. The peroxidases for the medicaments of the present invention may be extracted, by methods and techniques well known to those skilled in the art, from natural milieu, such as those peroxidases extracted from horseradish and saliva [for example, as described in Mansson-Rahemtulla et al., Biochemistry, 27:233–239 (1988)], as well as the lactoperoxidases extracted from milk derivatives (i.e., whey) and myeloperoxidases produced by leukocytes. These peroxidases also include those peroxidases (including myeloperoxidases) that are produced by recombinant DNA techniques, also well known to those skilled in the art.

[As utilized herein, the term "International Unit(s)" identifies that amount of the enzyme that will effect catalysis of 1 micromole of substrate per minute at pH 7 and 25° C. Enzymes are supplied in dry or liquid form with the label specifying the concentration in IU's on a per gram or per milliliter basis, as appropriate.]

lactoperoxidase is a glycoprotein which, in one commercial embodiment is a lyophilized powder derived from milk. This commercial peroxidase has an activity of 80 International Units (hereinafter sometimes referred to as IU's) and a projected molecular weight of 93,000 for L-Tyrosine Iodination. The physical-chemical properties reported for lactoperoxidase includes: a molecular weight of 78,000; partial specific volume 0.74; and heme/mole 1.0.

Salivary peroxidase is a glycoprotein which may be derived from the saliva or the acini of the parotid glands. The chemical characteristics of salivary peroxidase are not well known. However, the physical-chemical properties reported for salivary peroxidase includes a molecular weight ranging from approximately 80,000–100,000.

Myeloperoxidase is also a glycoprotein. In one commercial embodiment (from SIGMA corp., St. Louis, Mo., U.S.A.), myeloperoxidase may be obtained from human leukocytes, being lyophilized from 0.02 M sodium acetate buffer. This commercial embodiment has an activity of 40–100 I.U.'s.

Horseradish peroxidase is a glycoprotein. In one commercial embodiment (SIGMA, corp., St. Louis, Mo., U.S.A.), it is an essentially salt free powder. This commercial embodiment has an activity of 250–330 units per mg. solid. Preliminary studies of this embodiment have indicated the presence of two basic and no acidic isoenzymes therein. [As utilized herein, the term "unit" refers to that amount of the horseradish peroxidase that will form 1.0 mg purpurogallin in 20 sec. at pH 6.0 at 20° C. This purpurogallin (20 sec.) unit is equivalent to approx. 18 uM units per min. at 25° C.]

Examples of the preferred peroxidase/substrate combinations to utilize in the medicament of the present invention are set forth below in Table IA:

TABLE IA

| Peroxidase | Substrates |
| --- | --- |
| (1) Salivary peroxidase | thiocyanate, iodide |
| (2) Lactoperoxidase | thiocyanate, iodide |
| (3) Myeloperoxidase | chloride, iodide, thiocyanate |
| (4) Horseradish peroxidase | chloride, iodide |
| (5) Plant peroxidase | chloride, iodide, bromide |

The reactions of representative enzyme systems from Table IA (in the presence of a peroxide—which for purposes of illustration herein, will be hydrogen peroxide—from the oxygen donor) to produce either a hypohalite or hypothiocyanite compound, are set forth in Table IB, as follows:

TABLE IB (1a) Salivary peroxidase catalyzes the interaction of thiocyanate and hydrogen peroxide to produce hypothiocyanite and water;
(1b) Salivary peroxidase catalyzes the interaction of iodide and hydrogen peroxide to produce hypoiodite and water;
(2a) Lactoperoxidase catalyzes the interaction of thiocyanate and hydrogen peroxide to produce hypothiocyanite and water;
(2b) Lactoperoxidase catalyzes the interaction of iodide and hydrogen peroxide to produce hypoiodite and water;
(3a) Myeloperoxidase catalyzes the interaction of chloride and hydrogen peroxide to produce hypochlorite and water;
(3b) Myeloperoxidase catalyzes the interaction of iodide and hydrogen peroxide to produce hypoiodite and water;
(3c) Myeloperoxidase catalyzes the interaction of thiocyanate and hydrogen peroxide to produce hypothiocyanite and water;

TABLE IB-continued (4a) Horseradish peroxidase catalyzes the interaction of chloride and hydrogen peroxide to produce hypochlorite and water;
(4b) Horseradish peroxidase catalyzes the interaction of iodide and hydrogen peroxide to produce hypoiodite and water;
(5a) Plant peroxidases catalyze the interaction of chloride and hydrogen peroxide to produce hypochlorite and water;
(5b) Plant peroxidases catalyze the interaction of iodide and hydrogen peroxide to produce hypoiodite and water; and
(5c) Plant peroxidases catalyze the interaction of bromide and hydrogen peroxide to produce hypobromite and water.

The oxygen donor of the present invention provides (supplies) the peroxide (for example, hydrogen peroxide) in the medicament necessary for oxidation of the substrate.

Preferably, the oxygen donor is an enzymatic system including a substrate, an enzyme specific to such substrate and other necessary reactants, such as water and/or oxygen and/or hydrogen. Alternatively, microorganisms, such as the Steptococci and Lactobacilli that are commonly referred to as lactic acid bacteria may be utilized in the medicaments of the present invention to supply the peroxide (in the form of hydrogen peroxide). Specific examples of such lactic acid bacteria include *Lactobaccillus casei* and *Streptococcus faecalis* and *Streptococcus mutans*. Use of such microorganisms (microbes) is especially preferred in the medicaments formulated for use as a vaginal cream for topical application.

It is also contemplated herein that inorganic peroxides (such as sodium peroxide and magnesium peroxide) or organic peroxides (such as benzyl peroxide and urea peroxide) may be utilized. Also, chemicals that, upon reaction, produce hydrogen peroxide may be utilized. Indeed, even hydrogen peroxide itself may be utilized as the oxygen donor. The precise oxygen donor to be utilized will vary depending upon several factors, including the formulation into which the medicament is to be made for administration.

Most preferably, the oxygen donor is an enzymatic system including an oxidizable substrate, an oxidoreductase enzyme specific to such substrate and other necessary reactants, such as oxygen, and/or water. Examples of such oxidizable substrates, and oxidoreductase enzymes specific therefor, include those enumerated in U.S. Pat. No. 4,564,519 issued to Pellico et al. (hereinafter referred to as Pellico '519). Such examples are set forth below in Table IIA:

TABLE IIA

| Oxidizable Substrate | Oxidoreductase Enzyme | Other Reactants |
| --- | --- | --- |
| (a) B-D-glucose | glucose oxidase | Water, Oxygen |
| (b) D-galactose | galactose oxidase | Oxygen |
| (c) urate | urate oxidase | Water, Oxygen |
| (d) choline | choline oxidase | Oxygen |
| (e) D-amino acids[1] | D-amino acid oxidase | Water, Oxygen |
| (f) D-glutamate | D-glutamate oxidase | Water, Oxygen |
| (g) glycine | glycine oxidase | Water, Oxygen |
| (h) glycollate | glycollate oxidase | Water, Oxygen |
| (i) L-sorbose | L-sorbose oxidase | |
| (j) primary alcohol | alcohol oxidase | |
| (k) primary amine | amine oxidase | |
| (l) NAD(P)H | NAD(P)H oxidase | |

[1]D-amino acids includes D isomers of proline, methionine, isoleucine, alanine, valine and phenylalanine.

The reactions of representative enzyme systems from Table IIA to produce hydrogen peroxide are set forth in Table IIB.

TABLE IIB (a) Glucose oxidase catalyzes the interaction of Beta-D-glucose, water and oxygen to produce hydrogen peroxide and gluconic acid;
(b) Galactose oxidase catalyzes the interaction of D-galactose and oxygen to produce hydrogen peroxide and D-galacto-hexo-dialdose;
(c) Urate oxidase catalyzes the interaction of urate, water and oxygen to produce hydrogen peroxide, allantoin and carbon dioxide;
(d) Choline oxidase catalyzes the interaction of choline and oxygen to produce hydrogen peroxide and betaine aldehyde;
(e) D-amino acid oxidase catalyzes the interaction of D-amino acids, such as the D-isomers of proline, methionine, isoleucine, alanine, valine and phenylalanine together with water and oxygen to produce hydrogen peroxide, ammonia and the corresponding alpha-keto acids;
(f) D-glutamate oxidase catalyzes the interaction of D-glutamate, water and oxygen to produce hydrogen peroxide, ammonia and 2-oxoglutarate; and
(g) Glycine oxidase catalyzes the interaction of glycine, water and oxygen to produce hydrogen peroxide, ammonia and glyoxylic acid.

The characteristics of representative oxidoreductase enzymes identified in Table IIA, from specific sources, are recited in Pellico '519, which recitations relating to these characteristics are hereby incorporated herein as part hereof.

Most preferably, the peroxidase medicaments of the present invention include either lactoperoxidase or myeloperoxidase in combination with a thiocyanate (SCN—) substrate and of a glucose/glucose oxidase enzymatic system oxygen donor.

It is preferred that the above-mentioned peroxidase/substrate/peroxide systems be formulated into the prophylactic and therapeutic medicaments for "in vivo" use as a substantially self-contained system that may be applied or used substantially without depending upon the users naturally-occurring "in vivo" concentrations of substrate, oxygen donors, peroxidases or other ingredients.

It is noted that the effectiveness of the peroxidase medicaments of the present invention may be affected by the naturally-occurring environment in which the medicament is to be administered. For example, in the human mouth, the concentration of hydrogen peroxide varies as a direct function of biological production and salivary flow. When salivary flow is at a diminished level, either as a natural event or as an event arising out of certain types of medical treatment, the oral concentrations of various elements, such as potassium thiocyanate and peroxidase, will be correspondingly reduced. This, in turn, may be a limiting factor in the prophylactic or therapeutic effectiveness of the medicament when it is orally administered. Moreover, when the oral concentration of peroxidase is suppressed through diminished salivary flow, oral concentrations of hydrogen peroxide may increase to a threshold level, wherein the hydrogen peroxide can impede the effectiveness of peroxidase of the medicament.

Accordingly, it can be seen that the concentrations of the substrate, oxygen donor and peroxidase in the medicaments described above should be adjusted and controlled to harmonize hydrogen peroxide and peroxidase concentrations, so as to limit the hydrogen peroxide concentrations to levels which do not impede with the activity of the peroxidase.

[As utilized herein, the term millimole identifies that quantity in grams corresponding to the molecular weight of the medicament divided by one thousand.]

When the oxygen donor is hydrogen peroxide itself, it is generally present in the medicament of the present invention in an amount from about 2 to about 300 millimole per gram or per milliliter of medicament and, preferably, from about 3 to about 30 millimole per gram or per milliliter of medicament.

In the event the oxygen donor is an oxidizable substrate and an oxidoreductase enzyme specific to the substrate, then the oxidizable substrate is generally present in the peroxidase medicament in an amount from about 0.015 to about 0.6 millimole per gram or per milliliter of medicament and, preferably, from about 0.025 to about 0.1 millimole per gram or per milliliter of medicament. The oxidoreductase is generally present in the medicament in an amount from about 0.5 to about 500 IU's per gram or per milliliter of the medicament and, preferably, from about 1.0 to about 40 IU per gram or per milliliter of the medicament.

In the event the oxygen donor is an organic or inorganic peroxide, then such peroxide is generally present in the medicament in an amount from about 0.000006 to about 0.6 millimole per gram or per milliliter of medicament and, preferably, from about 0.00006 to about 0.06 millimole per gram or per milliliter of medicament.

The substrate is generally present in the medicament in an amount ranging from about 0.0000008 to about 0.01 millimole per gram or per milliliter of medicament and, preferably, from about 0.000008 to about 0.006 millimole per gram or per milliliter of medicament.

In the event that the substrate is a thiocyanate salt (a pseudo-halogen), then it is generally present in the medicament in an amount from about 0.0001 to about 0.01 millimole per gram or per milliliter of medicament and, preferably, from about 0.006 millimole per gram or per milliliter of medicament. Care should be taken in formulating the medicament, so as to avoid the use of metal compounds which inhibit or impair the effectiveness of the enzymes.

In the event that the substrate is a halogen, then it is generally present in the medicament in an amount from about 0.0000008 to about 0.008 millimole per gram or milliliter of medicament and, preferably, from about 0.000008 to about 0.004 millimole per gram or per milliliter of medicament.

The peroxidase is generally present in the medicaments in an amount from about 0.01 to about 50 IU per gram or per milliliter of medicament and, preferably, in an amount from about 0.2 to about 4.0 IU per gram or per milliliter of medicament.

It is noted that, if desired, the peroxidase medicament may be formulated for "in vivo" use as a system that relies upon certain naturally-occurring "in vivo" concentrations of any one or combination of compounds of the system for obtaining the peroxidase-generated antiviral compound.

The antiviral prophylactic and therapeutic qualities of the peroxidase medicaments of the present invention may be dependent on the concentration of compounds that are produced by the formulation of the medicament of the present invention. The produced concentrations of these compounds may vary between 1 micro molar and 100 millimolar, with concentrations of between 5 micro molar and 1 millimolar being preferred. For achieving this, the concentration of peroxidase units relative to the concentrations of the oxygen donor and/or of the substrate is able to be varied over a wide range.

The presence of water promotes the oxidation/reduction reactions of the peroxidase medicaments of this invention. Water is also a reactant in certain reactions. Thus, preferably, the use of water in formulating the said medicaments should be at a relatively low concentration in order to impart maximum stability and shelf life.

Where the products of the activated enzyme systems in the medicaments include a weak organic acid, it is advantageous to formulate the medicament with a buffering agent to neutralize the organic acid. A suitable buffering agent is sodium bicarbonate.

It is preferred that the peroxidase medicaments of the present invention be formulated, so as to have a pH that substantially approximates physiological pH. In particular, it is preferred that the medicaments of the present invention have a pH ranging from 4.5 to 6.5, with a pH of from 6 to 6.5 being especially preferred.

It is to be understood that to be formulated as a self-contained active medicament, the ingredients of the medicament must be formulated with at least some of the ingredients thereof being maintained chemically-separated from one another until the use thereof. For example, the peroxidase, oxygen donors (the oxygen donor enzymatic systems or the microorganisms) may be immobilized or microencapsulated, so that until the use thereof, they will not react with one another. If none of the substances of the systems described above are destroyed or inhibited by any ingredients, the medicament will have activity against enveloped viruses, including herpes simplex viruses and HIV's.

The peroxidase medicaments of the present invention may be formulated with a pharmaceutically-acceptable carrier in any suitable manner desired for administration in the particular situation. For example, the medicaments may be formulated as a dentifrice (such as a chewing gum, mouthwash, toothpaste, spray, lozenge or edible bonbon) for oral administration in the treatment of mouth infections. Alternatively, the medicaments may be formulated in a topical formulation (such as a spray, gel, cream, eye drops, shampoo, etc.) and/or incorporated in a bandage or a pad for topical administration to the skin, eyes, hair, etc., of individuals in need thereof. Finally, the medicaments may also be formulated as an injectable solution for internal application.

Formulations, equipment and processing techniques have been well developed and are well known in the art for preparing and packaging the medicaments of the present invention as either topical, oral or injectable formulations. The peroxidase/substrate/peroxide systems in the medicaments of this invention are adapted to be incorporated into these formulations. However, the enzymes described herein are subject to degradation and inactivation under conditions such as high shear and elevated temperatures. Accordingly, processing conditions should be controlled during the time span that the enzymes are being admixed with the other ingredients of the formulation of the medicaments and converted into finished products, so that the temperature does not rise above 55° C. for any extended period of time.

In order to enhance shelf stability, the admixture used in the preparation of the formulations of the peroxidase medicaments of the present invention should be substantially free of unbound water and the finished product should be packaged in a manner, so as to minimize exposure to air and moisture.

The peroxidase medicaments of the present invention will better understood by reference to the following examples, which are illustrative only and are not meant to be limiting in any manner:

EXAMPLE I

Illustrative base formulations for pharmaceutically-acceptable carriers for the peroxidase medicaments to be formulated with as a dentifrice for oral administration. Such as a chewing gum and chewable tablets and lozenges are set forth in Table III, as follows:

TABLE III

| Ingredients | Weight, Percent | | | |
|---|---|---|---|---|
| | (a) | (b) | (c) | (d) |
| Sorbitol, crystalline | 75 | — | 98 | 28 |
| Corn sugar | — | 75 | — | 70 |
| Gum base | 23 | 23 | — | — |
| Flavor | 1 | 1 | 1 | 1 |
| Color | 0.5 | 0.5 | 0.5 | 0.5 |
| Buffer | — | — | 0.5 | 0.5 |
| Saccharin, sodium | 0.005 | — | 0.005 | — |

In Table III, formulations (a) and (b) illustrate pharmaceutically-acceptable carriers in the form of chewing gum compositions while formulations (c) and (d) illustrate pharmaceutically-acceptable carriers in the form of tablet and lozenge compositions. Aspartame can be substituted for sodium saccharin in these formulations.

The following examples show varying ingredients and concentration levels which can be used in the preparation of dentifrices for providing the prophylactic and therapeutic effective amounts for oral administration according to the present invention:

TABLE IV

| | Weight, grams | | |
|---|---|---|---|
| | 4A | 4B | 4C |
| Chewing Gum | | | |
| Sorbitol, Crystalline | 70 | 70 | 70 |
| Gum base | 23 | 23 | 23 |
| Glycerol | 5 | 5 | 5 |
| Flavor | 1 | 1 | 1 |
| Color | 0.5 | 0.5 | 0.5 |
| Sodium Bicarbonate | 0.5 | 0.5 | 0.5 |
| | 100.0 | 100.0 | 100.0 |
| Peroxidase/Substrate/Peroxide System (per 100 g. chewing gum) | | | |
| Glucose oxidase | 40,000 IU | — | — |
| B-D glucose | 1.0 g | — | — |
| Choline oxidase | — | 8,000 IU | — |
| Choline | — | 1.0 g | — |
| D-glutamate oxidase | — | — | 2,500 IU |
| D-glutamate | — | — | 0.1 g |
| Lactoperoxidase | 4,000 IU | 1,500 IU | 1,000 IU |
| Potassium thiocyanate | 0.01 g | 0.005 g | — |
| Sodium thiocyanate | — | — | 0.01 g |

TABLE V

| | Weight, grams | | |
|---|---|---|---|
| | 5A | 5B | 5C |
| Chewing Gum | | | |
| Sorbitol, Cryst. | 43 | 43 | 43 |
| Gum Base | 20 | 20 | 20 |
| Glycerol | 25 | 25 | 25 |
| Flavor | 1 | 1 | 1 |
| Color | 0.5 | 0.5 | 0.5 |
| Sodium Bicarbonate | 0.5 | 0.5 | 0.5 |
| | 100.0 | 100.0 | 100.0 |

TABLE V-continued

| | Weight, grams | | |
|---|---|---|---|
| | 5A | 5B | 5C |
| Peroxidase/Substrate/Peroxide System (per 100 g chewing gum) | | | |
| D-Amino acid oxidase | 5,000 IU | — | — |
| D-Alanine | 0.1 g | — | — |
| Glucose oxidase | — | 20,000 IU | 2,000 IU |
| B-D-Glucose | — | 0.5 g | 0.5 g |
| Lactoperoxidase | 500 IU | 2,500 IU | 1,000 IU |
| Potassium thiocyanate | — | 0.01 g | 0.005 g |
| Sodium thiocyanate | 0.01 g | — | — |
| Sodium ascorbate | — | 0.01 g | — |

TABLE VI

| | Weight, grams | | |
|---|---|---|---|
| | 6A | 6B | 6C |
| Lozenge | | | |
| Sorbitol, Crystalline | 97 | 97 | 97 |
| Glycercol | 1 | 1 | 1 |
| Flavor | 1 | 1 | 1 |
| Color | 0.5 | 0.5 | 0.5 |
| Sodium Bicarbonate | 0.5 | 0.5 | 0.5 |
| | 100.0 | 100.0 | 100.0 |
| Peroxidase/Substrate/Peroxide System (per 100 g. lozenge) | | | |
| Glucose oxidase | 10,000 IU | — | — |
| B-D glucose | 1.0 g | — | — |
| Choline oxidase | — | — | 2,000 IU |
| Choline | — | — | 0.5 g |
| Urate oxidase | — | 10,000 IU | — |
| Urate | — | 0.75 g | — |
| Lactoperoxidase | 200 IU | 200 IU | 1,500 IU |
| Potassium thiocyanate | — | — | 0.01 g |
| Sodium thiocyanate | 0.05 g | 0.08 g | — |

TABLE VII

| | Weight, grams | | |
|---|---|---|---|
| | 7A | 7B | 7C |
| Lozenge | | | |
| Sorbitol, Crystalline | 80 | 80 | 80 |
| Corn sugar | 17 | 17 | 17 |
| Flavor | 1 | 1 | 1 |
| Color | 0.5 | 0.5 | 0.5 |
| Sodium Bicarbonate | 0.5 | 0.5 | 0.5 |
| | 100.0 | 100.0 | 100.0 |
| Peroxidase/Substrate/Peroxide System (per 100 g. lozenge) | | | |
| Glucose oxidase | — | 5,000 IU | 1,000 IU |
| B-D glucose | — | 0.5 g | 1 g |
| D-glutamate oxidase | 10,000 IU | — | — |
| D-glutamate | 0.05 g | — | — |
| Lactoperoxidase | 1,500 IU | 2000 IU | 1,000 IU |
| Potassium thiocyanate | 0.001 g | 0.005 g | — |
| Sodium thiocyanate | — | — | 0.005 g |

EXAMPLE II

Illustrative base formulations for pharmaceutically-acceptable carriers for the peroxidase medicaments of the present invention to be formulated as a topical medicament for topical administration, such as a cream, a gel or to be incorporated in a bandage or pad, are set forth in Table VIII, as follows:

TABLE VIII

| | Weight, Percent | |
|---|---|---|
| Ingredients | (a) | (b) |
| Deionized water | 19.02 | 20.0 |
| Corn Starch[1] | 38.04 | — |
| Lubrajel DV[2] | 38.04 | — |
| Aloe vera | 0.000021 | — |
| Natrosol 250 M[3] | 0.1 | — |
| Xylitol | 4.76 | — |
| Cirami N.1[4] | — | 20.0 |
| Sunflower Oil | — | 40.0 |
| Vitamin E | — | 0.05 |
| Tensami 4/07[4] | — | 2.0 |
| Tensami 1/05[4] | — | 3.0 |
| Bronopol[4] | — | 2.0 |
| Myacide SP[4] | — | 2.0 |
| Propylene Glycol | — | 10.0 |

[1] An example of such a corn starch is the hydrogenated starch solution marketed under the name HYSTAR TPF by Alban Muller International, Montreuil, France.
[2] Lubragel DV is a Glycerine and acrylic soution marketed by Alban Muller International, Montreuil, France.
[3] Natrosol 250 M is a hydroxyethylcellulose marketed by Aqualon, Inc., of Hopewell, Virgina, U.S.A.
[4] Cirami N.1, Tensami 4/07, Tensami 1/05, Bronopoi and Myacide SP are all marketed by Alban Muller International, Montreuil, France.

In Table VIII, formulation (a) illustrates pharmaceutically-acceptable carriers in the form of a gel, and (b) illustrates pharmaceutically-acceptable carriers in the form of a cream.

The following Tables show varying ingredients and prophylactic and therapeutic effective amounts (quantities) which can be used in the preparation of topical peroxidase medicaments, according to the present invention:

TABLE IX

| | Weight, grams | |
|---|---|---|
| Ingredients | 9A | 9B |
| Gel | | |
| Deionized water | 19.03 | 19.03 |
| Corn Starch | 38.054 | 38.054 |
| Lubrajel DV | 38.054 | 38.054 |
| Aloe vera | 0.001 | 0.001 |
| Natrosol 250 M | 0.1 | 0.1 |
| Xylitol | 4.76 | 4.76 |
| | 100.00 | 100.00 |
| Peroxidase/Substrate/Peroxide System (per 100 g Gel) | | |
| Glucose oxidase | 10,000 IU | — |
| B-D Glucose | 1.0 g | — |
| Choline oxidase | — | 8,000 IU |
| Choline | — | 1.0 g |
| Lacteroperoxidase | 200 IU | 1,500 IU |
| Potassium thiocyanate | — | 0.005 g |

TABLE IX-continued

| Ingredients | Weight, grams | |
|---|---|---|
| | 9A | 9B |
| Sodium thiocyanate | 0.05 g | — |

TABLE X

| Ingredients | Weight, grams | | |
|---|---|---|---|
| | 10A | 10B | 10C |
| Cream | | | |
| Deionized Water | 21.51 | 21.51 | 21.51 |
| Cirami N. | 20.0 | 20.0 | 20.0 |
| Sunflower Oil | 40.0 | 40.0 | 40.0 |
| Vitamin E | 0.04 | 0.04 | 0.04 |
| Tensami 4/07 | 2.0 | 2.0 | 2.0 |
| Tensami 1/05 | 3.0 | 3.0 | 3.0 |
| Bronopol | 2.0 | 2.0 | 2.0 |
| Myacide SP | 2.0 | 2.0 | 2.0 |
| Propylene Glycol | 10.0 | 10.0 | 10.0 |
| | 100.00 | 100.00 | 100.00 |
| Peroxidase/Substrate/Peroxide System (per 100 g Cream) | | | |
| Glucose oxidase | 5,000 IU | — | — |
| B-D glucose | 0.5 g | — | — |
| D-Amino acid oxidase | — | 5,000 IU | — |
| D-Alanine | — | 0.1 g | — |
| Urate oxidase | — | — | 10,000 IU |
| Urate | — | — | 0.75 g |
| Lactoperoxidase | 2,000 | 500 IU | 200 IU |
| Potassium thiocyanate | 0.005 g | — | — |
| Sodium thiocyanate | — | 0.01 g | 0.08 g |

EXAMPLE III

Illustrative formulations for pharmaceutically-acceptable carriers for the peroxidase medicaments of the present invention to be formulated as an eye wash solution for topical administration as an eye drop or an eye wash, are set forth in Table XI, as follow:

TABLE XI

| Ingredients | Weight, Percent | |
|---|---|---|
| | (a) | (b) |
| Sorbic Acid 0.0025% | — | 0.0002 |
| Purified Water | 99.4 | 98.1 |
| Boric acid | 0.018 | 0.0176 |
| Sodium Borate (Hydrated 10 H$_2$O) | 0.0015 | 0.0013 |
| Sodium chloride | 0.0025 | — |
| Benzalkonium chloride[1] | 0.0001 | — |
| Edetate disodium[1] | 0.001 | — |

[1]Benzalkonium chloride and Edetate disodium are added as preservatives.

The following Table shows the varying ingredients and the prophylactic and therapeutic effective amounts (quantities) which can be used in the preparation of eye wash medicaments, according to the present invention:

TABLE XII

| Ingredient | Amounts per 5 ml Eye Wash[1] |
|---|---|
| Glucose oxidase | 2,500 units[2] |
| Glucose | 20 milligrams |
| Lactoperoxidase | 150,000 ABTS units[3] |
| Potassium thiocyanate | 200 micrograms |

[1]The eye wash solution is a 5 ml solution of: 90 milligrams of Boric acid; 6.6 milligrams of hydrated sodium borate (10 H$_2$O); 2500 units Vitamin A and 0.125 ug of sorbic acid 0.0025%
[2]As utilized in this example, the term "unit" of Glucose oxidase identifies that amount of Glucose oxidase that oxidizes 3.0 milligram glucose to gluconic acid in one minute at pH 5.10 and 37° C. The assay conditions are set forth in Assay method FS 250 of Finnish Sugar Co. Ltd., of Finland. In this Example, 1 milligram of glucose oxidase has an activity of 100–120 units at 37° C. at pH 5.
[3]As utilized herein, the term "ABTS units" identifies that amount of lactoperoxidase that catalyzes the oxidation of 1 mM of the ABTS substrate [2,2'-Azino-bis (3-Ethylbenzthiazoline-6-Sulfonic Acid)] in one minute at pH 5 and 37° C. The assay conditions are set forth by Mansson-Rahemtulla, B., et al., Biochemistry, Vol. 27, at pages 233–239 (1988). In this Example, 1 milligram of lactoperoxidase has an activity of 600 ABTS units at 37° C. and 5 pH.

The composition is formulated separately in two parts, which, before application, are combined and shaken to dissolve and mix the two parts.

The first part is a mixture of the lactoperoxidase and the glucose oxidase. The second part is a 5 ml solution of the boric acid, hydrated sodium borate (10 H$_2$O), vitamin A, 0.0025% sorbic acid, potassium thiocyanate, water and glucose. The 5 ml solution (the second part) is mixed with the first part and shaken to dissolve the powder. Administration may be made as normal eye drops.

EXAMPLE IV

An illustrative base formulation for a pharmaceutically-acceptable carrier for the peroxidase medicaments to be formulated as an injectable composition (solution) for internal (injectable) administration. The base composition is a buffer solution (pH 7) of 0.15 molar sodium chloride and 60 millimolar sodium phosphate. To this composition 30 units of myeloperoxidase is added and the solution is mixed to form the medicament. [As utilized in this Example, a unit refers to that quantity of the enzyme necessary for catalyzing the increase of 1 unit of absorbance at 470 nm in one minute at room temperature using auto-dianisidine, see Krawicz. et al., *Gastroenterology*, vol. 87, pps. 1344–1350 (1984). In this context, 1 microgram equals 1 units].

A prophylatic or therapeutic effective amount (for example, approximately 0.5 ml) of this medicament is then administered to a patient in need thereof. Preferably, this administration will be by intramuscular injection.

It is noted that this same solution may be used as a spray when nebulized as normally authorized.

EXAMPLE V

This example shows the effectiveness of the peroxidase/substrate/peroxide system of the peroxidase medicament of the present invention against an enveloped virus and, in particular, against herpes simplex virus-1. The peroxidase/substrate/peroxide system of the peroxidase medicaments was prepared having the formulation set forth in Table XIII below:

TABLE XIII

| Ingredient | Amounts per 100 ml buffer solution[1] |
| --- | --- |
| Glucose oxidase | 0.02 milligrams |
| Glucose | 1.20 millimoles |
| SCN- | 0.06 millimoles |
| Lactoperoxidase | 4.00 milligrams |

[1]The buffer solution is a Hank's-Balanced Salt Solution that is calcium, magnesium and glucose free. The pH of the buffer solution is 7.4. The weights of the contents of the HBSS buffer solution is as follows, for every 1000 ml of distilled water: 8 grams NaCl; 0.4 grams KCl; 0.06 grams $Na_2HPO_4$; and 0.06 grams of $KH_2PO_4$.

Four (4) strains of HSV-1 viruses were collected from exsudates of herpetic lesions on tongue, nasopharyngeal cavity and vulva. These samples were pooled then typed as HSV-1 using immunofluorescence. They were subsequently allowed to multiply in MRC5 cells and growth medium. Separation from cells and cell debris was performed by centrifugation. Viruses were then stocked in aliquots in liquid nitrogen.

Samples from the HSV-1 pool were then diluted from ten to ten fold down to the antepenultimate cytotoxic titre which was taken as base line for each experiment or control.

The peroxidase formulation set forth above in Table XV was then mixed with an equal volume of the HSV-1 pool suspension at the base line titre (1 ml/1 ml).

These virus and the peroxidase formulation mixtures were allowed 30, 60 or 120 minutes incubation at 37° C. They were then diluted from 10 to 10 fold to obtain suspensions at 5 exponentially decreasing concentrations. Of each of these suspensions, 50 microliters were sampled to inoculate a layer of fibroblasts grown "in vitro".

After inoculation, the cell cultures were examined daily up to seven days. Marks of cytotoxicity were semiquantitatively quoted, as follows: 1+ being from 0 to 25%; 2+ being from 25 to 50%; 3+ being from 50 to 75%; 4+ being from 75 to 100%.

Controls were settled by substituting the oxidizing moiety with an equal volume of the HBSS buffer. On the contrary, blanks held the complete oxidative system of the formulations but the virus moiety was replaced by the growth medium.

The cytotoxity of pretreated virus was compared with that of suspensions which had not been in contact with the peroxidase formulation. This comparison allowed to express the results in terms of:

1. no effect: that is, no difference of cytotoxity between experiments and controls;
2. delaying effect: when a minimum 24 hour delay lengthened the lag phase before the onset of cytotoxity;
3. inhibiting effect: when a complete inhibition of the virus cytotoxity was noticed.

Twenty samples of the HSV-1 pool, were dispersed each into five (5) consecutive dilutions (from $10^{-4}$ to $10^{-8}$) which were treated by mixing in the peroxidase formulations. These tests were compared with the equivalent number of controls which yield the results plotted in FIG. 1.

Figure 1:
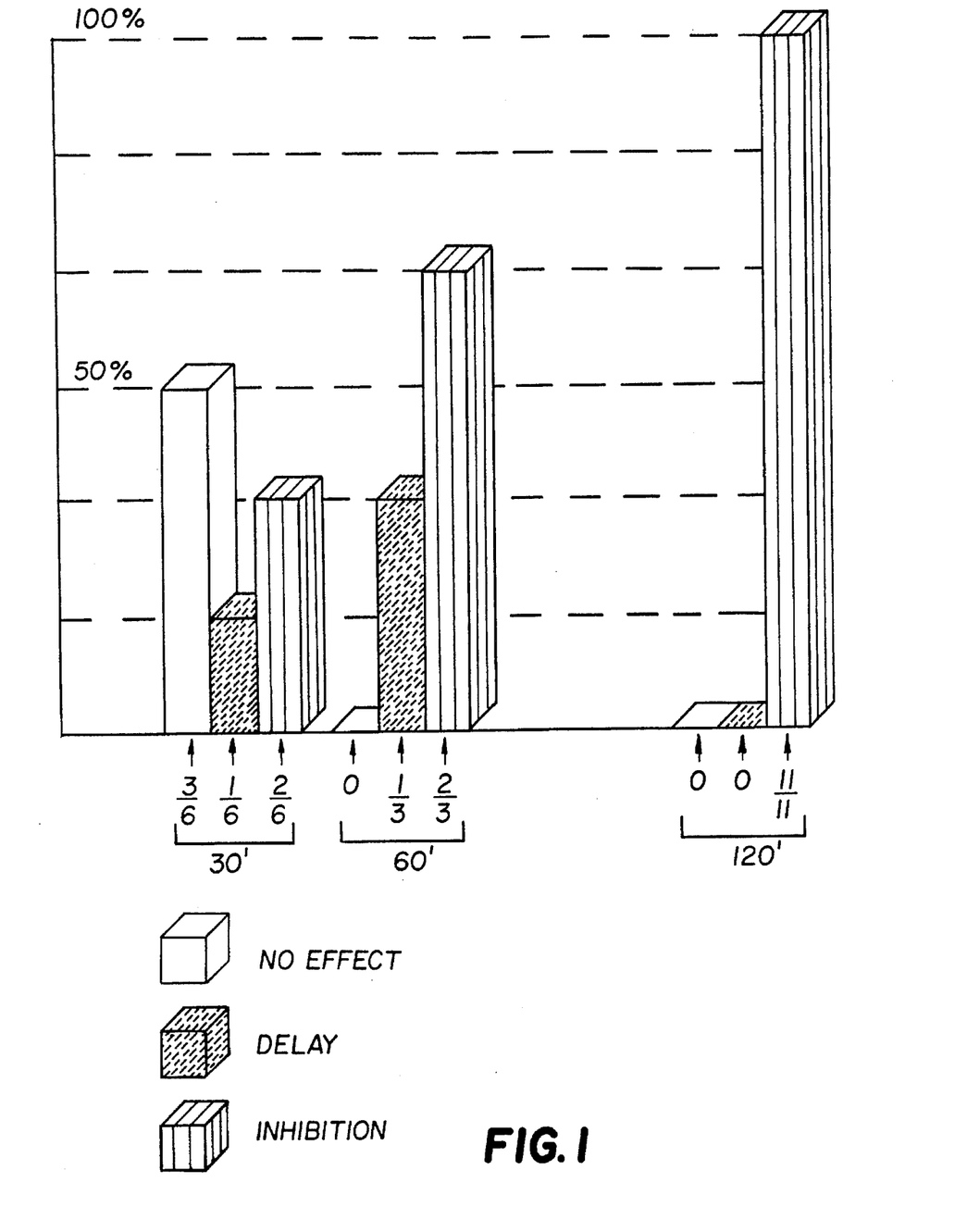
FIG. 1 is a bar chart diagrammatically representing the results obtained after 20, 30 and 120 minutes of pretreatment of HSV-1 with the peroxidase/thiocyanate/hydrogen peroxide system of the medicaments of the present invention.

As can be seen by reference to FIG. 1, a one hundred and twenty (120) minute incubation period in the presence of the peroxidase formulation induced complete inhibition of HSV-1 cytotoxic potential. Sixty (60) and thirty (30) minutes of incubation yield ⅔ and ⅓ of complete inhibition, ⅓ and ⅙ delaying effect, respectively. However, ½ of the samples which had sustained thirty (30) minutes incubation with the oxidase formulation, showed no loss of cytotoxicity.

A direct toxicity on the fibroblast layers, due to the oxidative moiety, could not be avoided in a few cases, when assaying the highest concentration (H) of the mixtures. This toxicity, however, was not found while using the ensuing dilutions (that is from $H \times 10^{-1}$), so that it did not disturb the reading of viral toxicity itself.

The results nonetheless disclose an obvious weakening of the viruses cytotoxicity power which appears to be time dependent.

EXAMPLE VI

This example shows the effectiveness of the peroxidase/substrate/peroxide system of the peroxidase medicaments of the present invention against an enveloped virus and, in particular, against human immunodeficiency virus. The peroxidase/substrate/peroxide system of the peroxidase medicaments was prepared having the formulation set forward in Table XIV below:

TABLE XIV

| Ingredient | Amounts per 100 ml buffer solution[1] |
| --- | --- |
| Glucose oxidase | 0.02 milligrams |
| Glucose | 1.20 millimoles |
| SCN- | 0.06 millimoles |
| Lactoperoxidase | 4.00 milligrams |

[1]The buffer solution is a Hank's-Balanced Salt Solution that is calcium, magnesium and glucose free. The pH of the buffer solution is 7.4. The weights of the contents of the HBSS buffer solution is as follows, for every 1000 ml of distilled water: 8 grams NaCl; 0.4 grams KCl; 0.06 grams $Na_2HPO_4$; and 0.06 grams of $KH_2PO_4$.

HIV aliquots were obtained from a supernatent of ARV-4 cell line. The aliquots were then extemporaneously mingled with an equal volume of the peroxidase formulation set forth in Table XIV and incubated from 1 hour down to 2 minutes at 37° C.

HIV plus the peroxidase formulation was then inoculated to phytohaemagglutinin-stimulated human lymphocyte cultures. Final dilution of the aliquots were 1:20, 1:100 and 1:200. Controls were obtained by preincubating the virus in the buffer alone. The cultures were supplied again with fresh lymphocytes on day 11 (arrows in FIG. 2). Virus growth was monitored with an ELISA detecting p24 either intra-cellular (per $10^6$ cells) or in the supernatant.

In control experiments, the virus produced early intracellular p24 when inoculated to human lymphocytes, at final dilutions 1:20 and 1:100. Dilution 1:200 however yielded both delayed and lower amounts of p24. By contrast, virus treated with the peroxidase formulation only produced low amounts of p24 at dilution 1:20. The results of these experiments are summarized and can be seen with reference to FIGS. 2 and 3.

Fifteen (15) days lymphocyte culture yielded 90 pg of p24 per $10^6$ in controls inoculated with 1:200 diluted virus, while 25 pg only were detected after innoculation of virus treated within the peroxidase formulation for one (1) hour and diluted 1:20. With higher dilutions, no p24 was detected in $10^6$ cells. But the whole culture of $10^7$ cells had nevertheless been contaminated by infectious particles since p24 had been shed later on into the supernatant.

Cytopathic effect brought forth by the virus in control experiments was not observed after treatment of lymphocytes with the peroxide formulation alone. By contrast, leaving SCN- out the mixture (and therefor allowing $H_2O_2$ accumulation), proved to be cytotoxic at the lowest dilution (1:20).

Kinetic experiments were preformed with preincubation at 2, 10, 20, 30 and 60 minutes. These showed that 2 minutes contact with the undiluted peroxidase formulation was enough to reduce the HIV infectivity exhibited in the samples.

EXAMPLE VII

This example also shows the effectiveness of the peroxidase/substrate/peroxide system of the peroxidase medicaments of the present invention against an enveloped virus and, in particular, against human immunodeficiency virus. The peroxidase utilized in this example is purified human recombinant myeloperoxidase.

An MPO-MIX was prepared. This MPO-MIX included 500 ul of culture medium (RPMI, Gibco and 5% fetal calf serum, Seralab), supplemented with sodium thiocyanate (20 ug/ml), glucose 1%, glucose oxidase (6 mU/ml) and from 10 to 40 ug/ml of purified human recombinant myeloperoxidase. This human recombinant myeloperoxidase was produced utilizing the method described in patent application no. PCT/EP89/00668. However, it is to be understood that this myeloperoxidase may be obtained from any suitable source.

A 60 ul viral suspension of HTLVIIIB virus, derived from infected Molt3 cells, i.e., 1200 $TCID_{50}$ (Tcells infectious dosis 50%) is prepared.

Finally, $2.10^6$ reporter Sup T1 cells are obtained. In particular, supT1 cells, derived from a human lymphoma (J. Hoaxie, Univ. of Pennsylvania, Philadelphia, Pa. U.S.A.) were utilized.

The standard procedure was performed as follows:

The HTLVIIIB viral suspension (60 ul) was added to the MPO-MIX (500 ul) and the resulting mixture was incubated for 15 minutes at 37° C. The mixture was then transferred onto a Sup T1 cell pellet (containing $2.10^6$ cells) and further incubated for 30 minutes at 37° C. with gentle stirring. Cells were then washed twice with culture medium RPMI and fetal calf serum), pelleted and resuspended in 10 ml of the same culture medium, i.e., at a cell density of $2.10^5$ cells/ml. These resuspended cells were then cultivated at 37° C. for ten (10) days.

Microscopic examination (monitoring) of the cultures was done at days 3, 5 and 7 to record cytopathic effects, such as the formation of syncitia. On day 10, 450 ul of the cell culture was collected. This 450 ul of the cell culture was then mixed with 50 ul of buffered saline containing 10% Triton X-100 and stored at −20° C. before us. The samples were subsequently analyzed by ELISA to quantify the p24 HTLVIIIB antigen (the viral progeny). More precisely, the chosen ELISA measures the amount of HTLVIIIB p24 protein and uses as primary antibody a murine monoclonal antibody raised against p24 (Dupont, U.S.A.) and, as secondary antibody, human anti HTLVIIIB immunoglobulins labelled with biotin. Specific complexes were revealed using a streptavidin-norse radish peroxidase conjugate (Amersham) and the OPDA chromogenic substrate (Sigma). Optical densities were read at 490 nm.

The results of these experiments are set forth below in Table XV. These results show that the peroxidase medicament of the present invention containing human recombinant myeloperoxidase at concentrations ranging from 10 to 40 ug/ml, completely inhibits the replication of the HTLVIIIB virus.

TABLE XV

| Test | | Days of Culture Following exposure of virus to rMPO | | | | |
|---|---|---|---|---|---|---|
| | | 0 | 3 | 5 | 7 | 10 |
| 1. Virus HTLVIIIB + MPO-MIX (10 ug/ml MPO) | CPE[1] ELISA[2] | nd nd | — 15 | — 18 | — 19 | nd 13 |
| 2. Virus HTLVIIIB + MPO-MIX (20 ug/ml MPO) | CPE[1] ELISA[2] | nd nd | — 26 | — 23 | — 18 | nd 19 |
| 3. Virus HTLVIIIB + MPO-MIX (40 ug/ml MPO) | CPE[1] ELISA[2] | nd nd | — 20 | — 14 | — 17 | nd 13 |
| 4. Virus HTLVIIIB alone | CPE[1] ELISA[2] | nd nd | (+) 73 | + 170 | ++ 354 | nd 1000 |
| 5. SupT1 cells + MPO-MIX (40 ug/ml MPO) (no HTLVIIIB) | CPE[1] ELISA[2] | nd nd | — 18 | — 23 | — 19 | nd 16 |
| 6. Virus HTLVIIIB + MPO-MIX (40 ug/ml MPO) (no Glucose Oxidase) | CPE[1] ELISA[2] | nd nd | (+) 87 | + 115 | ++ 193 | nd 835 |
| 7. Virus HTLVIIIB + MPO-MIX (no MPO) | CPE[1] ELISA[2] | nd nd | (+) 115 | + 394 | ++ 658 | nd 800 |

[1]CPE (Cytopathic effects):
− means no syncitia was observed.
± means a few small syncitia was observed.
+ −> ++ means an increase in the number and size of syncitia was observed.
[2]ELISA: are expressed in milli units $OD_{490}$ As can be from Table XV, in samples 1, 2 and 3 no syncitia was observed and inhibition of viral replication was noted. Sample 4 exhibited positive control: both syncitia and viral replication were observed. Sample 5 exhibited negative control: no virus in the assay. In Sample 6 the MPO enzyme lacked one of its substrates ($H_2O_2$). Thus, no effect on viral replication was noted. Finally, in sample 7, since there was no MPO in the assay, no effect on viral replication was observed.

The sum total of the above assays is to demonstrate that use of myeloperoxidase, in appropriate concentrations, in the peroxidase system of the medicament of the present invention completely inhibits the replication of HTLVIIIB virus.

EXAMPLE VIII

This example demonstrates the anti-viral effectiveness of the lactoperoxidase/substrate/peroxide system and of the myeloperoxidase/substrate/peroxide system against genital herpes in the general herpes guinea pig model (the intravaginal guinea pig model).

20 female Hartley guinea pigs received an intravaginal innoculation of $10^5$ pfu of HSV2 MS virus. Beginning with day 4 and thereafter continuing daily until day 24, these guinea pigs were monitored for the appearance and development of herpes lesions (based on a scale from 0 to 4) and were treated by use of one of the three following gels:

1. A control gel (for a group of four guinea pigs) prepared having the formulation set forth for the gel only the example 9A of Table IX;

2. A gel containing a lactoperoxidase/substrate/peroxide system (for a group of eight guinea pigs) prepared having the formulation set forth in example 9A of Table IX, except that 88 IU of lactoperoxidase (per 100 g of gel) was utilized and not 200 IU of lactoperoxidase;

3. A gel containing a myeloperoxidase/substrate/peroxide system (for a group of eight guinea pigs) prepared having the formulation set forth in example 9A of Table IX, except that 70.8 IU of myeloperoxidase (per 100 g of gel) was utilized and not 200 IU of lactoperoxidase;

The development of herpes lesions occurs in two successive phases: the first phase (primary infection) is due to the innoculated virus; and the second phase (recurrences) is due to the reactivation, more or less frequent. Of the virus present in the nerve cells in a laten form.

The treatment consisted of applying 0.6 grams of gel on the herpes lesions appearing around the external genital organs. The results of these experiments are summarized in Table XVI (wherein the effect of the treatments on the primary infection are summarized) and in Table XVII (wherein the effect of the treatments on the recurrences are summarized) and can be seen with reference to the graph set forth in FIG. 4.

TABLE XVI

| Gel | Average Severity[1] | Average Maximal Score | Average Duration of Primary Infection |
|---|---|---|---|
| 1 | 12.7 | 2.5 | 11 |
| 2 | 7.4 p 0.02[2] | 1.8 p 0.03[2] | 6.5 p 0.01[2] |
| 3 | 8.4 p 0.02[2] | 1.9 p 0.01[2] | 7.9 p 0.05[2] |

[1]Severity = The sum o the scores from day 4 to day 12
[2]Significant according to the Student's Test

TABLE XVII

| Gel | Average Number of Recurrences[1] | Average Duration of a Recurrence (in days) |
|---|---|---|
| 1 | 1.5 | 4.3 |
| 2 | 1.4 N.S.[2] | 3 N.S.[2] |
| 3 | 1.9 N.S.[2] | 3.3 N.S.[2] |

[1]These is a recurrence if one measures, during two successive days, a score equal to 0.5 (erythma) or, during one day, at least one score equal to one (vesicule). A recurrence is preceeded and followed by a day without lesions.
[2]Not significant according to the Students Test.

Figure 4:
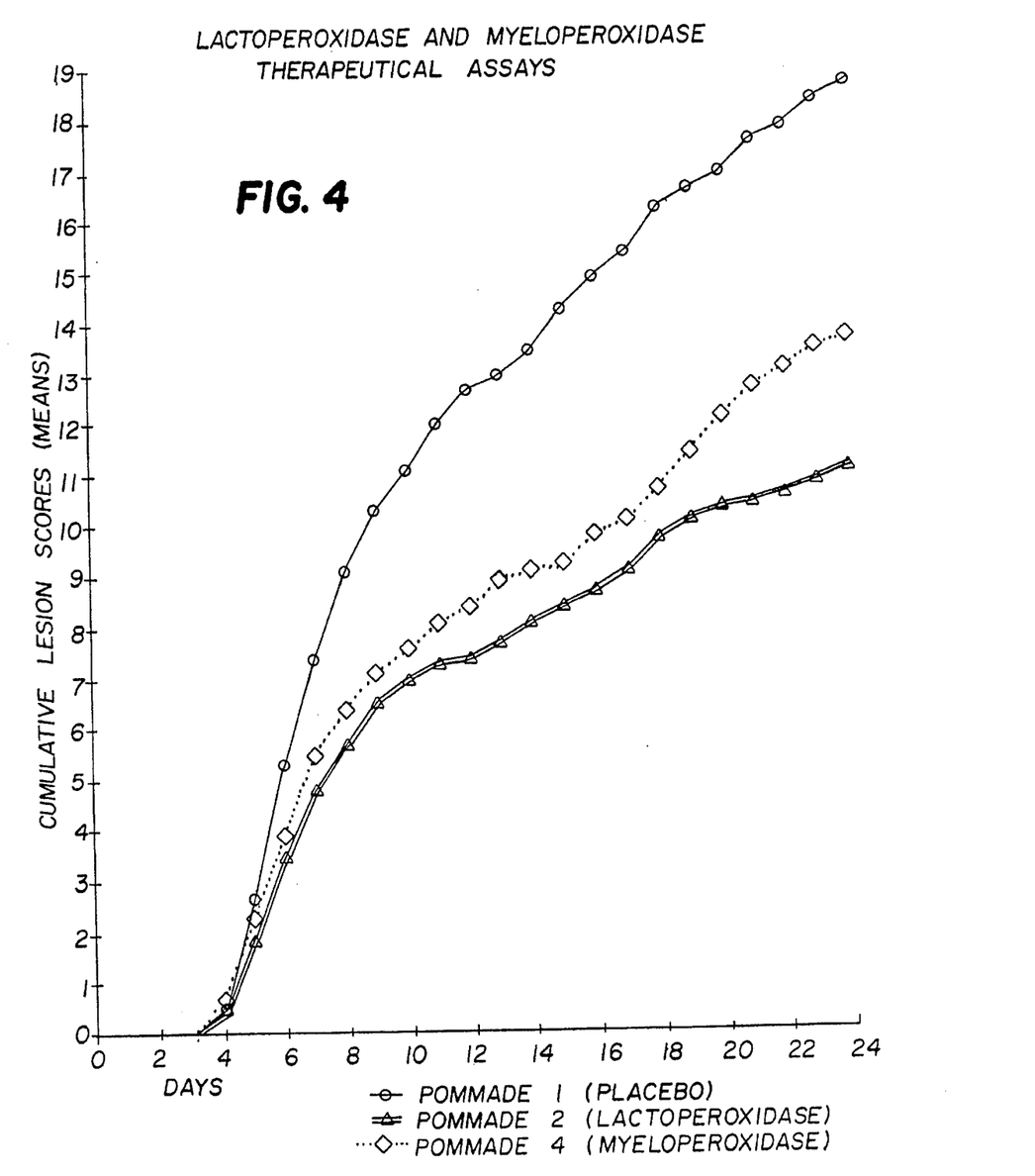
FIG. 4 is a line chart diagrammatically illustrating the results of lactoperoxidase and myeloperoxidase assays.

As can be seen from Table XVI and from FIG. 4, lesions from the primary infections were generally severe (maximal score 2.5–3) and persisted from day 4 to days 12–14, while lesions from the recurrences were relatively benign (maximal score 0.5–1) and disappeared after 3–4 days on average. The results of these treatments clearly show that the gels containing the lactoperoxidase or the myeloperoxidase significantly reduce the severity, the maximal scores and the duration of the primary infection.

Figure 2:
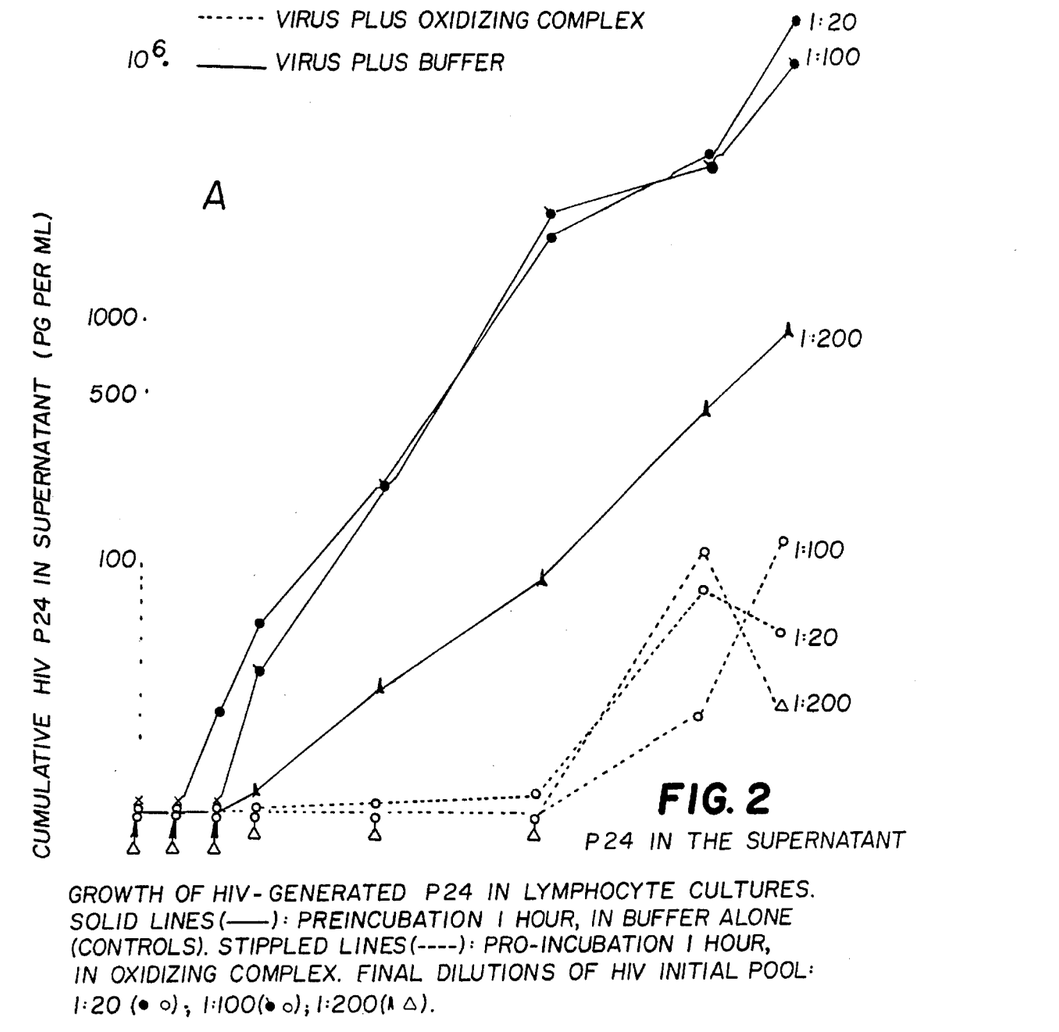
FIG. 2 is a line chart diagrammatically representing the results obtained of growth of HIV-generated p24 in lymphocyte cultures in the supernatant after treatment with the peroxidase/thiocyanate/hydrogen peroxide system of the medicaments of the present invention.
Figure 3:
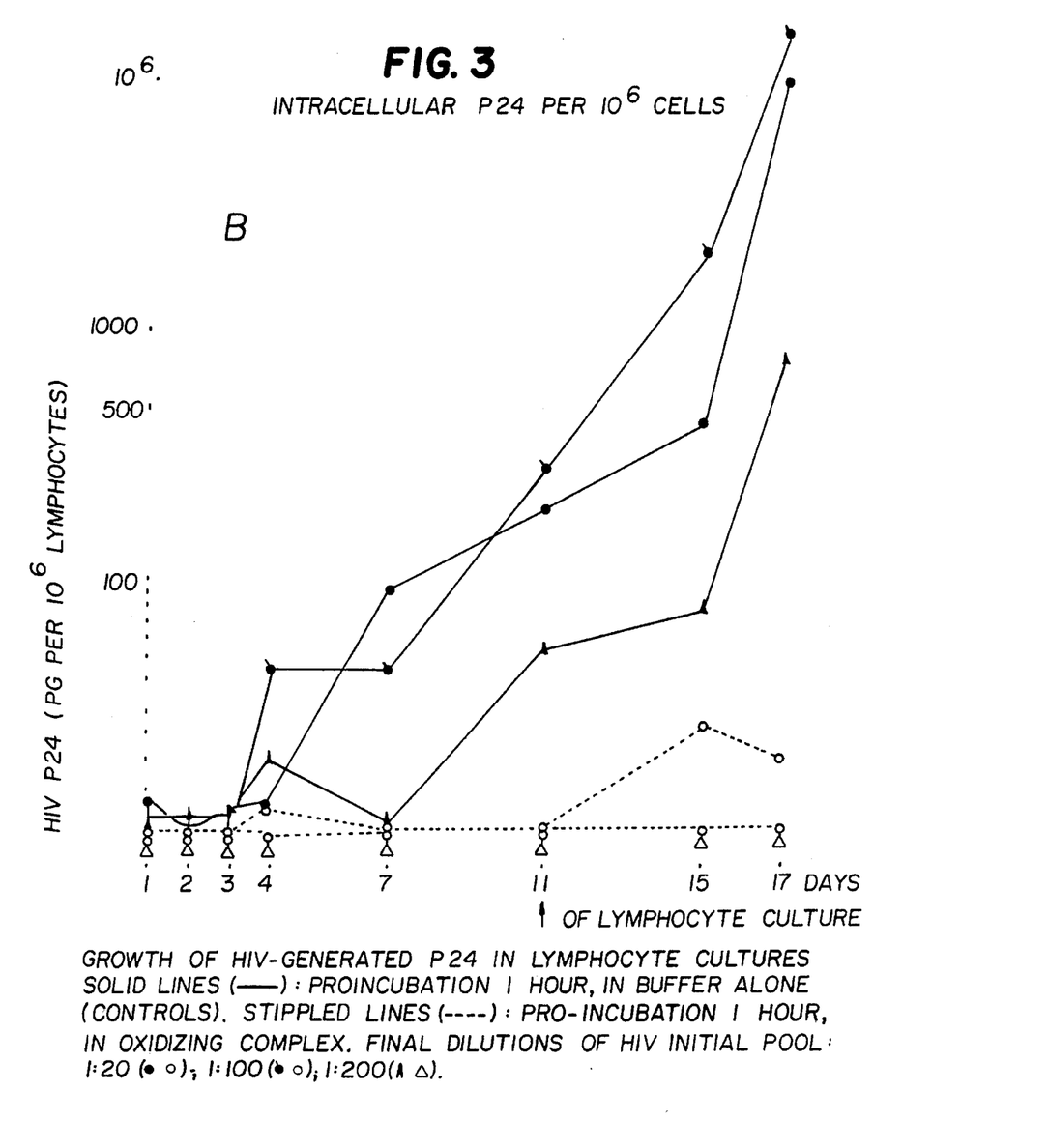
FIG. 3 is a line chart diagrammatically illustrating the results obtained of intracellular growth of p24 per 10-cells after treatment with the peroxidase/thiocyanate/hydrogen peroxide system of the medicaments of the present invention.

KEY TO FIGS. 2 AND 3

FIG. 2 is illustrative of the growth of HIV-generated p24 in lymphocyte cultures by measurement of the p24 in the supernatant. FIG. 3 is illustrative of the growth of HIV-generated p24 in lymphocyte cultures by measurement of intracellular p24 per $10^6$ cells.

Symbols utilized in FIGS. 2 and 3 are as follows: Solid lines (—): preincubation 1 hour, in buffer alone (controls); Stppled lines (- - -): preincubation 1 hours, in oxidizing complex. Final dilutions of HIV initial pool: 1:20 (•○); 1:100 (■□); and 1:200 (▲△).

In view of the foregoing description and examples, it will become apparent to those of ordinary skill in the art that equivalent modifications thereof may be made without departing from the spirit and scope of this invention.

We claim:

1. A method of treating or preventing the spread of herpes simplex virus infections which comprises administering to an individual in need thereof, in combination with a pharmaceutically acceptable carrier, a therapeutically effective amount of a composition comprising a non-conjugated peroxidase in association with an oxygen donor and an oxidizable substrate for which the peroxidase is specific, wherein the non-conjugated peroxidase is selected from the group consisting of myeloperoxidase and lactoperoxidase.

2. The method of claim 1 wherein the non-conjugated peroxidase is myeloperoxidase.

3. The method of claim 1 wherein the non-conjugated peroxidase is lactoperoxidase.

4. The method of claim 1 wherein the non-conjugated peroxidase is myeloperoxidase and the oxidizable substrate is chosen from the group consisting of chloride, bromide, iodide and thiocyanate salt.

5. The method of claim 1 wherein the non-conjugated peroxidase is lactoperoxidase and the oxidizable substrate is chosen from the group consisting of a iodide and thiocyanate salt.

6. The method of claim 1 wherein the oxygen donor is a lactic acid bacteria and the pharmaceutically acceptable carrier is a vaginal cream for topical application.

7. The method of claim 1 wherein the composition is substantially free of unbound water.

8. The method of claim 1 wherein the oxygen donor is an enzymatic system including a substrate and an enzyme specific for the substrate, such that hydrogen peroxide is formed thereby.

9. The method of claim 1 wherein the oxygen donor is an enzymatic system including glucose and glucose oxidase.

10. The method of claim 1 wherein the oxygen donor is an inorganic peroxide.

11. The method of claim 1 wherein the oxygen donor is an organic peroxide.

12. The method of claim 1 wherein the substrate is a thiocyanate salt, the oxygen donor is an enzymatic system including a glucose substrate and a glucose oxidase; and the peroxidase is myeloperoxidase.

13. The method of claim 1 wherein the substrate is a thiocyanate salt, the oxygen donor is an enzymatic system including a glucose substrate and a glucose oxidase; and the peroxidase is lactoperoxidase.

* * * * *